United States Patent [19]
Bales et al.

[11] Patent Number: 5,269,804
[45] Date of Patent: Dec. 14, 1993

[54] ENDOSCOPIC COLO-RECTAL BOWEL CLAMP

[75] Inventors: Thomas O. Bales, Coral Gables; Jurgen Kortenbach, Fort Lauderdale; Kevin W. Smith, Miami, all of Fla.

[73] Assignee: Symbiosis Corporation, Miami, Fla.

[21] Appl. No.: 780,076

[22] Filed: Oct. 21, 1991

Related U.S. Application Data

[63] Continuation-in-part of Ser. No. 680,392, Apr. 4, 1991, Pat. No. 5,192,298.

[51] Int. Cl.$^5$ .............................. A61B 17/00
[52] U.S. Cl. .................................... 606/205
[58] Field of Search .......... 128/749, 751; 606/205, 606/206, 207, 208, 190, 170, 167, 158, 157, 120

[56] References Cited

U.S. PATENT DOCUMENTS

| | | | |
|---|---|---|---|
| 2,397,823 | 4/1946 | Walter | 606/207 |
| 2,478,595 | 9/1949 | Richter | 606/207 |
| 3,895,636 | 7/1975 | Schmidt | 606/205 |
| 4,574,804 | 3/1986 | Kurwa | 606/207 |
| 4,669,471 | 6/1987 | Hayashi | 606/205 |

Primary Examiner—Lee S. Cohen
Assistant Examiner—Samuel Gilbert
Attorney, Agent, or Firm—David P. Gordon

[57] ABSTRACT

Disposable laparoscopic colo-rectal surgical bowel clamps for insertion through trocar tubes are disclosed. The instruments broadly include: a hollow aluminum tube; an aluminum clevis which is formed separately from the aluminum tube with the distal end of the hollow aluminum tube crimped around the proximal end of the clevis; axially off-set pivot pins coupled to the clevis; two bowel clamp blades each having a pivot hole through which the off-set pivot pin of the clevis is pivotally engaged, and each having another through-hole; an aluminum push rod extending at least partially through the hollow aluminum tube and apparatus for imparting reciprocal motion to the push rod relative to the aluminum tube, whereby the reciprocal motion is translated at an offset pivot of the clevis into high leverage pivotal motion of the blades. The blades are configured with bowed intermediate sections, and cutout proximal sections for the grasping and clamping of a bowel portion or other relatively large anatomical parts.

17 Claims, 10 Drawing Sheets

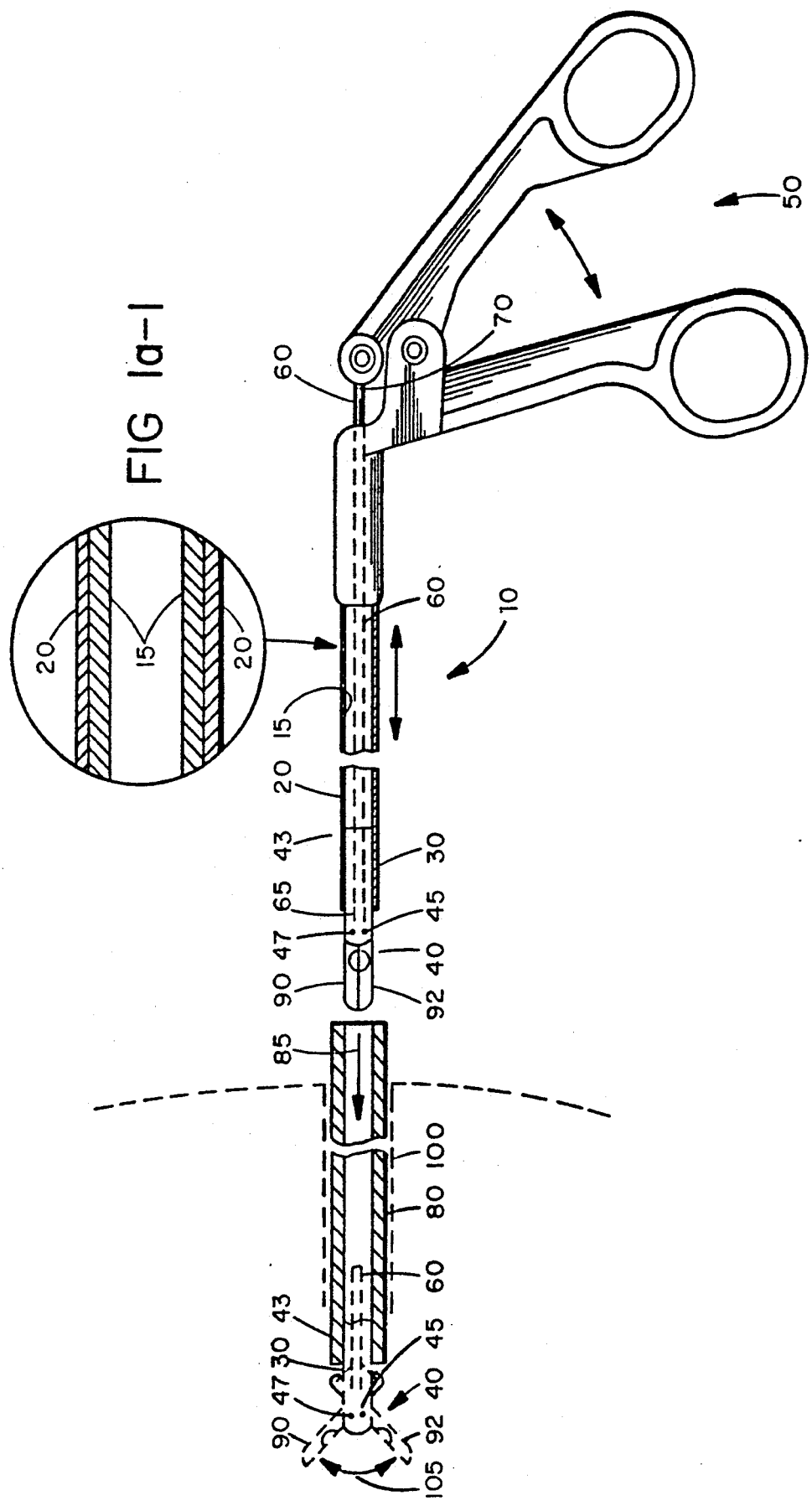

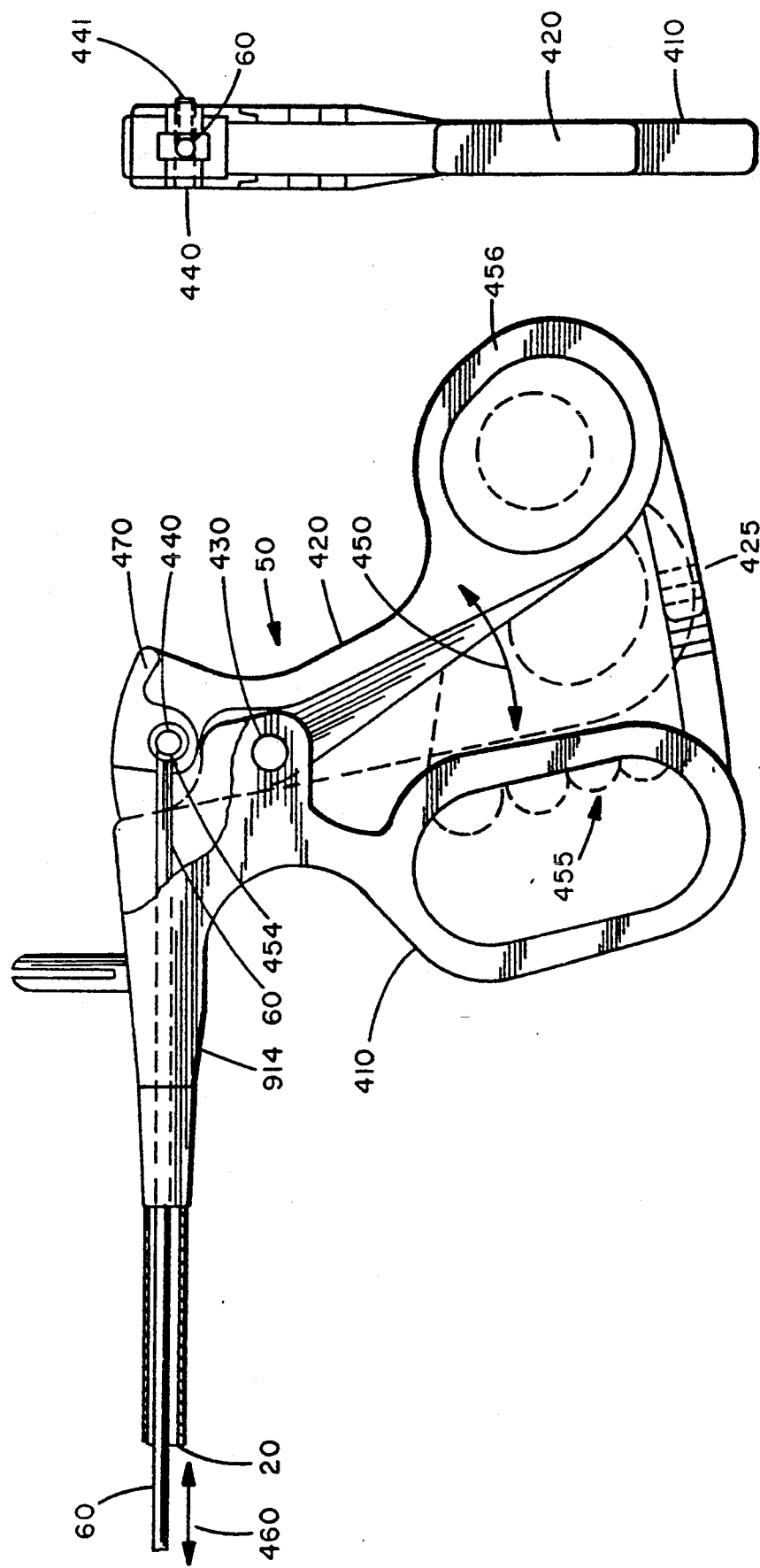

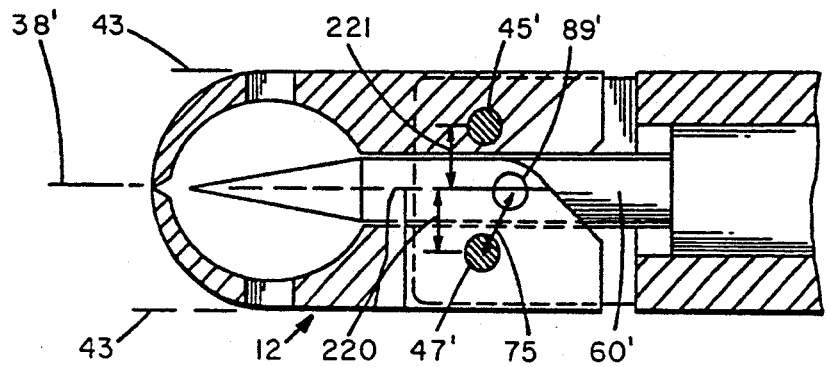
FIG. 4
PRIOR ART
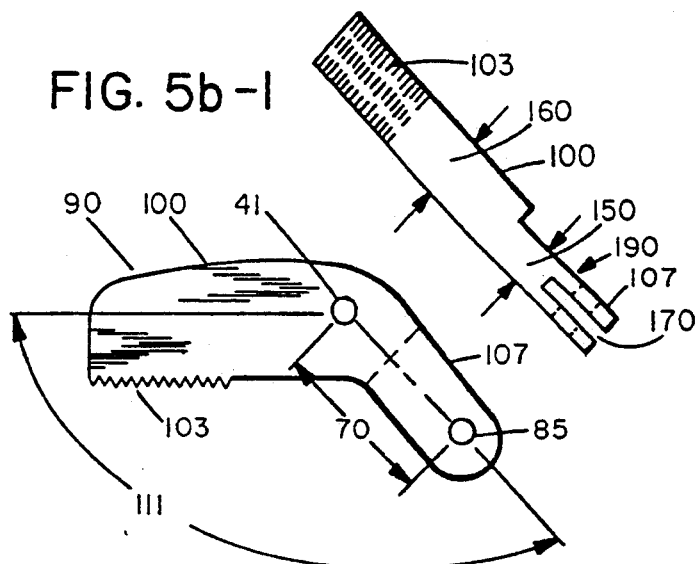
FIG. 5b-1
FIG. 5b
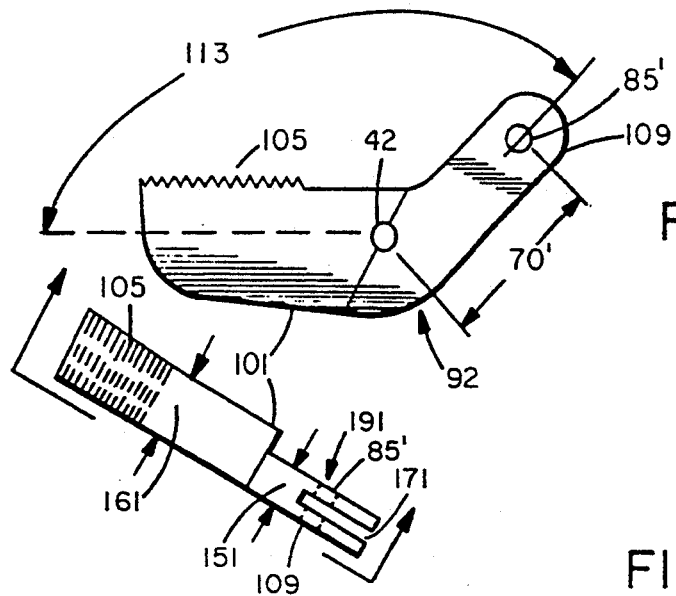
FIG. 5a
FIG. 5a-1

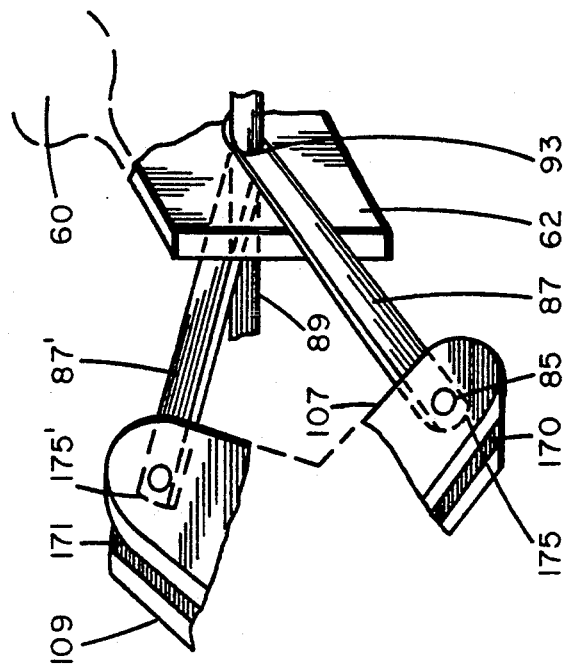
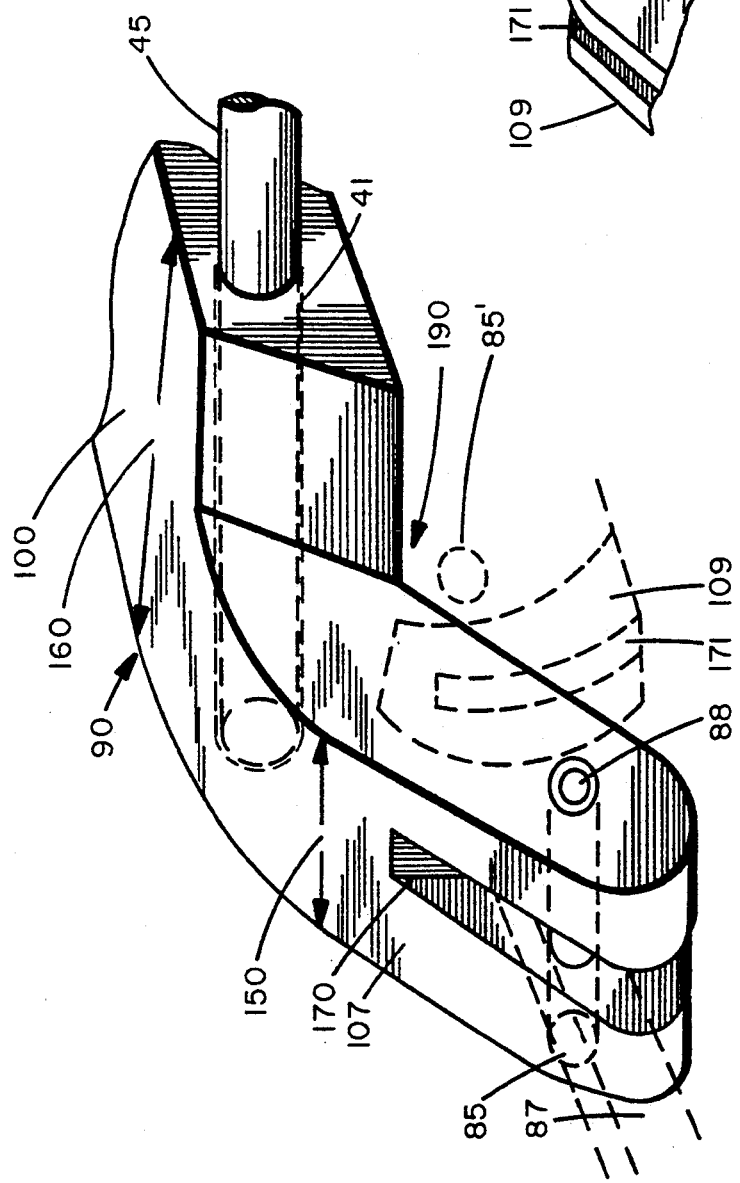
FIG. 9
FIG. 8

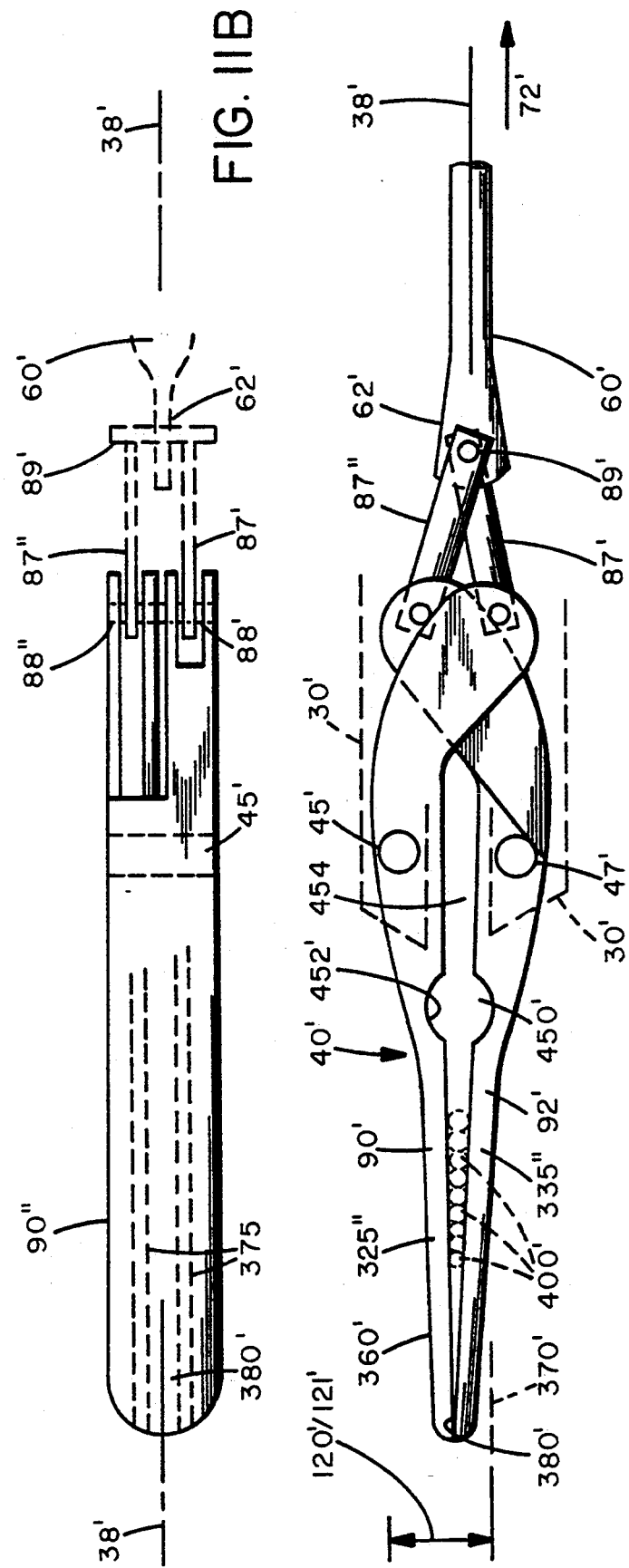

ENDOSCOPIC COLO-RECTAL BOWEL CLAMP

This is a continuation-in-part of U.S. Ser. No. 07/680,392, filed Apr. 4, 1991, now U.S. Pat. No. 5,192,298 which is hereby incorporated by reference herein in its entirety.

This application is related to U.S. Ser. No. 07/780,014 entitled "Double Acting, Dual Pivot Disposable Laparoscopic Surgical Instruments" assigned to the assignee hereof, now U.S. Pat. No. 5,171,258.

BACKGROUND OF THE INVENTION

The present invention broadly relates to endoscopic colo-rectal surgical instruments. More particularly, the invention relates to disposable surgical instruments which include disposable bowel clamps which are useful in a colo-rectal endoscopy procedure.

The (endoscropy) procedure has recently become a widely practiced surgical procedure. A laparoscopy procedure typically involves incising through the navel and through the abdominal wall for viewing and/or operating on the ovaries, uterus, gall bladder, bowels, appendix, although more recently, incisions and insertion of trocar tubes have been made in different areas of the abdomen and even in the chest cavity. Typically, trocars are utilized for creating the incisions. Trocar tubes are left in place in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Previous to the present invention, laparoscopic tools have utilized connecting mechanisms for imparting pivotal motion to the manipulating members of the end effectors. These tools, however, have utilized either single pivot mechanisms specifically designed to avoid protrusions outside of the outline of the laparoscopic tool so as to avoid any inadvertent contact with tissue of a patient, or double pivot mechanisms such as disclosed in U.S. Pat. No. 3,895,636 to Schmidt where the manipulating members are directly actuated by the axial movement of a common reciprocating member. While such tools have functioned adequately for many of their intended purposes, these laparoscopic tools have not enabled the desired amount of gripping or cutting force important in the manipulation of large vessels or organs, such as might be required in procedures involving, e.g., intestinal organs. As a result, no effective colo-rectal laparoscopic instruments have been available to date.

SUMMARY OF THE INVENTION

It is therefore an object of the invention to provide disposable laparoscopic surgical instruments particularly suited for surgical procedures involving larger organs, such as intestinal organs.

Another object of the invention is to provide disposable laparoscopic surgical instruments of improved design with high leverage end effectors and with connecting mechanisms of very small cross section which do not protrude outside of the envelope of the instrument.

It is a further object of the invention to provide a disposable laparoscopic surgical instrument which utilizes an improved linkage system which enables increased leverage to be applied to the manipulation members of the end effector of the instrument.

It is yet another object of the invention to provide a disposable laparoscopic colo-rectal bowel clamp.

In accord with the objects of the invention, a disposable laparoscopic colo-rectal bowel clamp generally includes: a tube; a push rod which extends through the tube; an actuating means engaging the tube and the push rod for imparting reciprocal axial motion to the push rod; bowel clamp blades coupled at their proximal ends to the push rod by connecting means which are also coupled to the push rod; a clevis coupled to the tube at its proximal end and to the bowel clamp blades at its distal end; and posts coupled to the clevis and extending through the bowel clamp blades such that the bowel clamp blades rotate thereabout, with the posts being transverse and displaced relative to the longitudinal axis of the tube, wherein axial movement of the push rod effects movement of the bowel clamp blades in a plane parallel to the longitudinal axis of the push rod.

Plastic shrink wrap is preferably utilized to electrically insulate the disposable instrument and extends over the aluminum tube and over at least an adjacent portion of the clevis. The tube and push rod are preferably made of aluminum, the clevis is preferably made of a high-strength aluminum alloy, the actuating means is preferably made of plastic and aluminum, and the bowel clamp blades are preferably made of 17/4 or 17/7 stainless steel.

The clevis of the invention is preferably a separately formed clevis having a knurled rod-like proximal end for mating with the end of the aluminum tube, and a U-shaped distal portion for supporting the posts which around which the bowel clamp blades rotate. A first post in the distal portion of the clevis is perpendicular to the legs of the U-shaped distal portion and transverse to the longitudinal axis of the aluminum tube and the push rod. The post is displaced from the longitudinal axis and arranged to extend through a hole in a first of the bowel clamp blades. The second transverse post is provided adjacent to and opposite the first post on the opposite side of the longitudinal axis. In this manner, the blades of the end effector bowel clamp are held by respective axially offset pivot posts and can respectively rotate around the posts. A high degree of leverage is thereby developed in the blades of the bowel clamp.

According to one aspect of the invention, the push rod is flattened on its distal end, and the linkage means which couple the push rod and the bowel clamp blades both extend through a hole in the flattened end of the push rod as well as through other holes in the proximal ends of the bowel clamp blades. Because the outer tube is positioned at a fixed distance from the rotation hole in the end effector (due to the clevis), when the push rod is moved axially relative to the tube, the end effectors (blades) cannot move axially. However, because the push rod is also a fixed distance away from holes in the proximal ends of the blades (due to the connecting means), movement of the push rod relative to the tube causes rotation of the blades in a plane. In other words, movement of the push rod relative to the tube causes the holes through the blades through which the linkage members extend to rotate along arcs centered at the rotation holes in the blades through which the transverse posts extend. Movement in this manner typically effects a clamping action.

In accord with another aspect of the invention, because of the shape and the material of the blades, once the blades have been brought into contact with each other at their distal ends, additional force on the blades caused by additional force on the push rod will cause the outwardly bowed intermediate sections of the blades to flatten.

A better understanding of the disposable laparoscopic colo-rectal surgical bowel clamp instrument of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable laparoscopic instrument prior to insertion into a trocar tube, and, in partial phantom format, after insertion into a trocar tube;

FIG. 1a-1 is a cross section through FIG. 1 at the indicated location thereof;

FIG. 2b is a cross-section view of the device of FIG. 2a;

FIG. 2d is a perspective view of the clevis elements shown in FIG. 2a;

FIG. 3a is a partially broken-away side elevation view of the actuating handle of the disposable laparoscopic instrument of the invention;

FIG. 3b is a rear elevation view of the device of FIG. 3a;

FIG. 4 is a side elevation view of a prior art instrument;

FIGS. 5a and 5b are side views, and FIGS. 5a-1 and 5b-1 are top views of the elements of device of FIG. 5;

FIG. 8 is a partial perspective view of a manipulation member of an end effector;

FIG. 9 is a partial perspective view of the linkage shown in FIG. 5;

FIGS. 11a and 11b show a laparoscopic colo-rectal bowel clamp of the present invention for grasping and sealing organ such as intestines and the like.

DETAILED DESCRIPTION OF THE PREFERRED EMBODIMENT

Figure 2B:
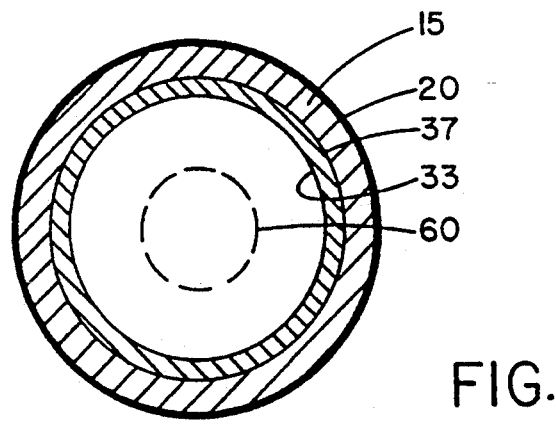

With reference to FIGS. 1 and 1a-1, a disposable laparoscopic surgical instrument is indicated at 10. The disposable laparoscopic surgical instrument 10 includes an aluminum tube 15 surrounded by a peripheral insulating shrink wrap layer of plastic 20, a clevis means 30, end effectors 40, actuating means 50, and a push rod 60. The clevis means 30 is advantageously a separately formed aluminum piece which fixedly engages aluminum tube 15 as described in more detail hereinafter. The clevis 30 also engages the manipulating members 90, 92 of the end effector 40 which are respectively pivotally engaged to clevis 30 at pivot pins 45, 47 as hereinafter more particularly described. End effector 40 is preferably formed of investment cast bronze as disclosed in copending U.S. Ser. No. 07/521,766 which was previously incorporated by reference herein, or can be formed of investment cast stainless steel, other metals, or plastic as desired. The push rod 60, which is also preferably formed of stainless steel, is engaged at its distal end 65 to the end effector 40, as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the manipulation members, e.g. blades or graspers 90, 92 of the end effector 40, in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the manipulating members, e.g. blades 90, 92 can be opened and closed as indicated at 105 by reciprocal motion of push rod 60 which results from operation of the manual actuating means 50. As is discussed more fully hereinafter, the clevis effectively translates the reciprocal motion of the push rod 60 into the end effector means action indicated at 105.

Figure 2A:
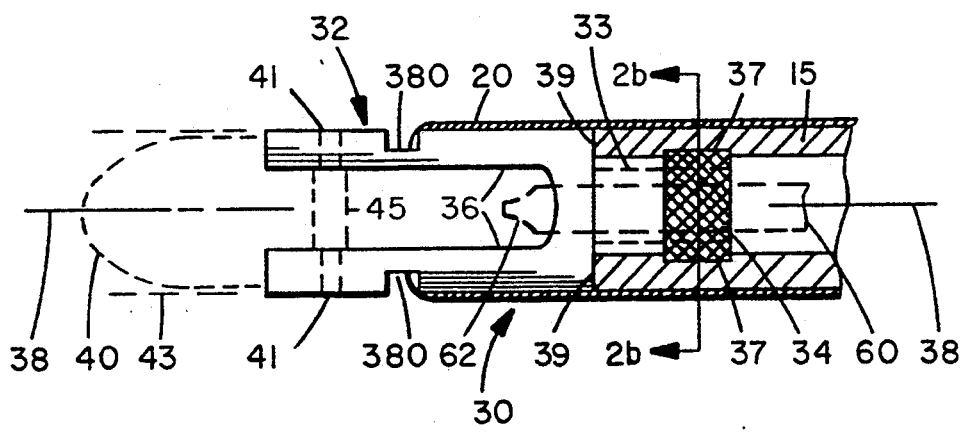
FIG. 2a is a side elevation view, partly in section, of the clevis of the invention in conjunction with the distal end of the tube and shrink wrap of the invention.
Figure 2C:
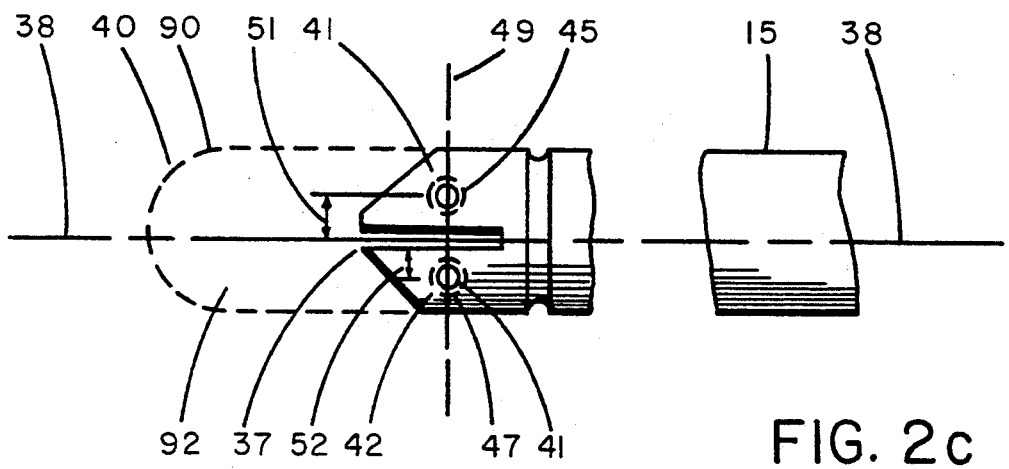
FIG. 2c shows the device of FIG. 2a rotated by 90°.
Figure 2D:
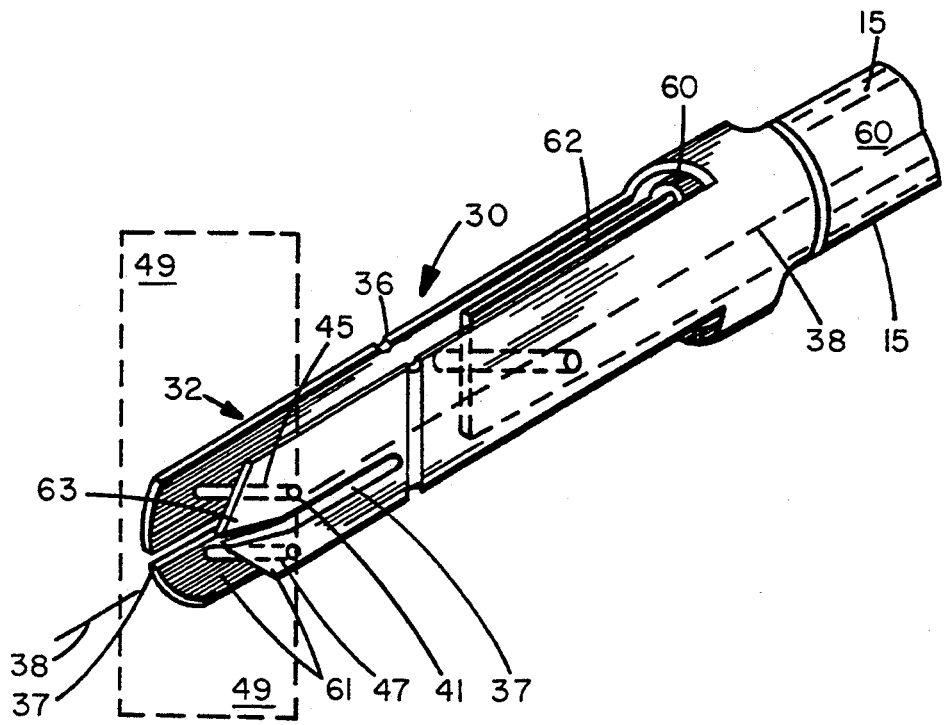

Turning to FIGS. 2a, 2b, 2c and the perspective view of FIG. 2d, a preferred configuration of the clevis 30 of the present invention is seen. The clevis has a knurled rod-like proximal portion 34 for mating with the end of the aluminum tube 15, and a post-supporting U-shaped distal portion 32 for holding the end effector means. The proximal portion 34 of the clevis is preferably hollow, as indicated at 33, to permit the push rod 60, with its flattened terminal portion 62 to extend therethrough. The distal portion 32 of the clevis 30 is provided with a first post or pivot pin 45, a second post or pivot pin 47, and legs 36, which have slots 137 to increase their flexibility and to allow independent adjustment of the two pivot posts 45 and 47. The posts 45, 47 are generally perpendicular, i.e. transverse, to the legs 36 of the clevis and are arranged to extend respectively through holes 41, 42 in the manipulation members 90, 92 of end effector means 40. In this manner, the blades or prongs 90, 92 of the end effector means 40 are held by, but can rotate around the posts 45, 47 (i.e. they are rotatably respectively engaged therewith) which are symmetrically disposed about longitudinal axis 38 and which are in a common plane which is transverse to longitudinal axis 38. Push rod 60, tube 15 and clevis 30 all have substantially the same common longitudinal axis 38. Posts 45, 47 are transverse to and displaced from axis 38 on opposite sides thereof as indicated at 51, 52 in FIG. 2c.

As seen in FIG. 2a, a recess or notch 380 is provided which extends across each leg 36 of the clevis 30. Consequently, a peripherally applied electrically insulating plastic wrap 20 can be end-cut at recess 380 and a smooth transition from the end effector means 40 via the clevis 30 to tube 15 can be achieved. Even if slight outward flaring of wrap 20 occurs at the end-cut, as is common, this flaring can be tolerated as it will be within the envelope of the normal outer instrument surface indicated at 43.

Clevis 30 is preferably made from a high strength aluminum base alloy (e.g. 2024 alloy of Alcoa) which is preferably harder than the aluminum base alloy (e.,g. 6061 or 6063 alloys of Alcoa) from which tube 15 is fabricated. The post elements 45, 47 portion of the clevis 30 may be made out of a high strength aluminum alloy or, for added strength, out of a stainless steel screw or nail. In assembly of the laparoscopy surgical instrument 10, serrated or knurled portion 34 of clevis 10 is fit snugly into tube 15 such that the walls of tube 15 abut the peripheral shoulder 39 of clevis 30, with the outer surface of tube 15 and the adjacent outer surface of clevis 30 having essentially the same diameter. Mechanical pressure is then applied to tube 15 peripherally at the location of knurled portion 34, thereby crimping the end portion of tube 15 onto the knurled portion 34. Mechanical pressure causes the projections of the knurls to bite into and firmly engage tube 15 as indicated at 37 due to the higher hardness of the clevis material. Alternately, the clevis may be pressed into the tube. Once the clevis 30 and tube-15 have been properly joined, the plastic shrink wrap 20 can be applied over the tube 15 and an adjacent portion of the clevis 30 and end-cut at recess 380. Alternately, the plastic shrink wrap may be applied after the end effectors are attached to the instrument by the posts as hereinafter described.

With reference to FIGS. 3a and 3b, manually operable actuating means are indicated at 50 which includes an electrically insulating housing 914 having a fixed handle portion 410 integral therewith and a lever portion 420 pivotally engaged to housing 914 at pivot pin 430. Push rod 60 passes through aluminum tube 15 (covered by shrink wrap 20) and engages cross pin 440 at 454; set screw 441 being used to extend into cross pin 440 and set push rod 60 in the cross pin 440. The cross pin 440 is fixedly positioned in lever member 420. Upon pivotal motion of lever arm 420, as indicated at 450, using a conventional hand grip as indicated at 455 to apply pressure to extended handle element 456 of lever member 420, push rod 60 will move linearly as indicated at 460 to actuate an end-effector (not shown in FIG. 4a) coupled thereto as hereinabove described. A customary, state-of-the art ratchet type holding mechanism is shown at 425 for locking lever portion 420 relative to handle 410.

Figure 5:
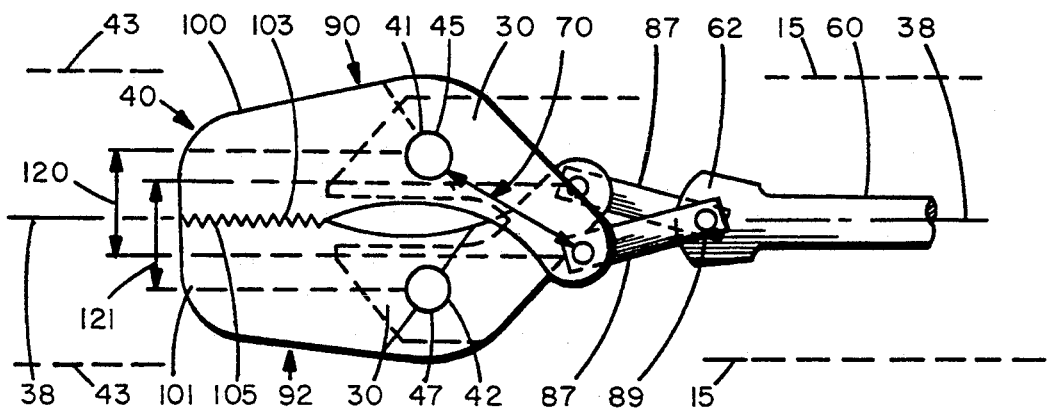
FIG. 5 is a side elevation view of the dual pivot instrument of the present in a closed position.

With reference to FIGS. 5, 5(A) 5(A)-1, 5(B) 5(B)-1, and 5(C), a preferred dual pivot end effector 40, in the form of a grasper, is shown. End effector 40 comprises manipulation members 90, 92 which are separately shown in FIGS. 5(A) and 5(A)-1, 5(B), and 5(B)-1. For the end effector 40, the manipulation members 90, 92 are essentially identical, with one being inverted 180° with respect to the other when arranged for operation in a laparoscopic instrument as shown in FIG. 5. Manipulation members 90, 92 each have an extended forward edged portion 100, 101, with opposed edges 103, 105 for grasping, cutting and the like. Base members 107, 109, integral with forward edged members are obliquely angled inwardly forward their associated edges 103, 105 as shown at 111, 113. Base member 107, 109 function as lever arms and are provided with through holes 41, 42 for respectively engaging pivot posts 45, 47 of clevis 30 which is shown in "phantom" in FIG. 5.

Figure 7:
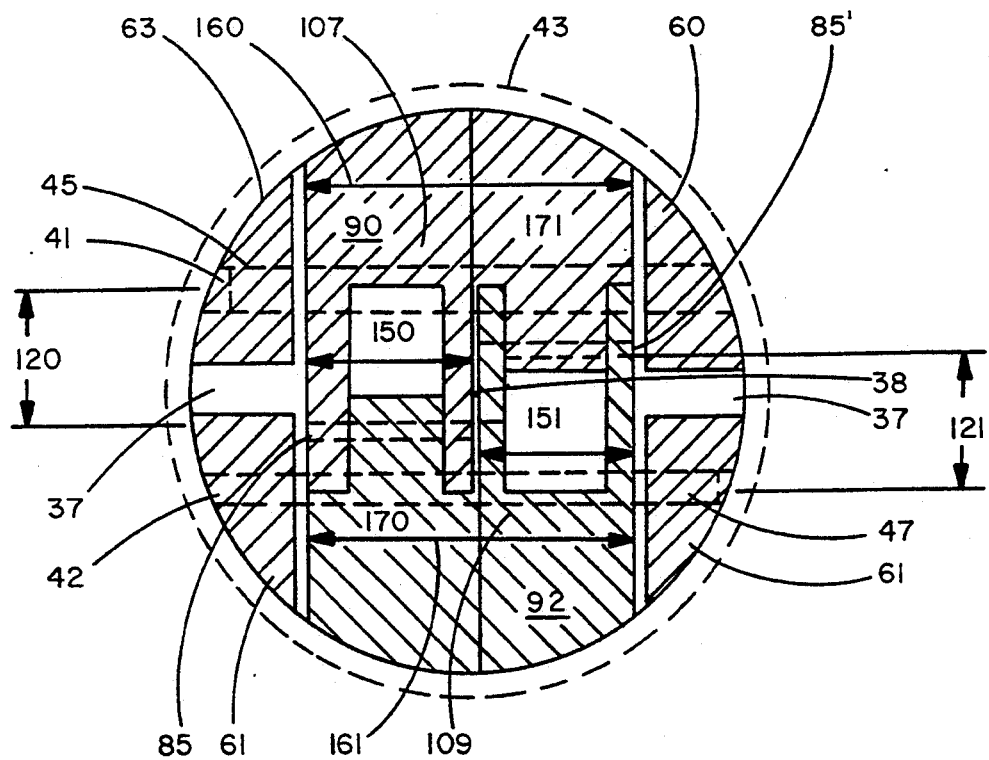
FIG. 7 is a rear sectional elevation view of the device of FIG. 6 along 7—7.

Posts 45, 47 are positioned transverse to longitudinal axis 38 of clevis 30, rod 60 and tube 15 as hereinabove described, and posts 45, 47 are each displaced radially outward and away from longitudinal axis 38 by the distances shown at 120, 121 in FIG. 5 and FIG. 7. The offset distances 120, 121 can be as large or larger than one-half of the diameter 43 of the instrument, and the longer the distances 120, 121, the greater the leverage that can be obtained and the greater the force that can be applied by the manipulation members 90, 92 end effector 40 to large organs and anatomic structures. Displaced posts 45, 47 of the device of FIG. 5 are suitably stainless steel screws which engage holes 41, 42 and are positioned directly opposite to each other in a common transverse plane on opposite sides of the longitudinal axis 38 and are suitably respectively engaged at about the midpoint of clevis quadrant segments 61, 63 shown in FIG. 2d and FIG. 7 which are separated by axial slots 37.

Figure 5C:
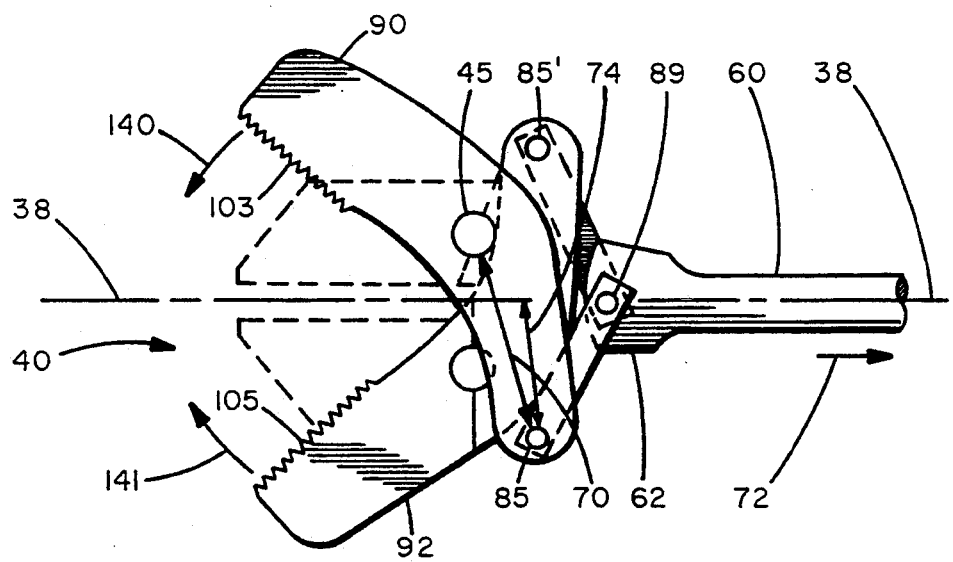
FIG. 5c is a side elevation view of the device of FIG. 5 in an open position.
Figure 6:
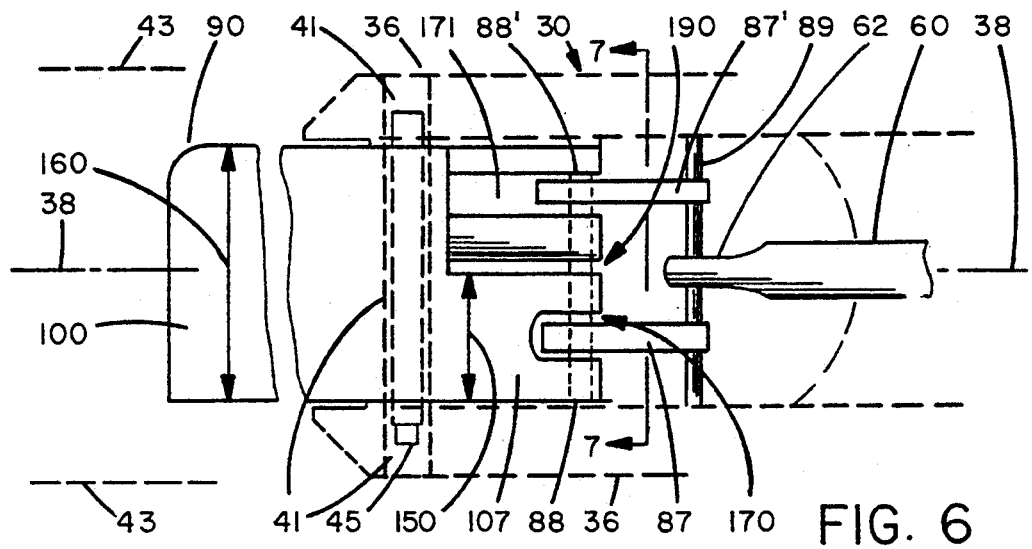
FIG. 6 is a plan view of the device of FIG. 5.

The provision of two separate axially displaced pivot posts 45, 47 for the respective manipulation members 90, 92 in accordance with the present invention establishes a lever arm indicated at 70 in the end effector "open" position of FIG. 5c when push rod 60 is moved in the axial direction indicated at 72. Lever arm 70, for manipulation member 90, is the distance from pivot 45 to the through hole 85 in member 90 which pivotally engages linkage means 87. Linkage means is suitably a thin metal bar e.g. stainless steel, to which flattened portion 62 of push rod 60 is pivotally engaged. Engagement is obtained by transverse pivot rod 89 which passes through hole 93 of metal linkage bar 87.

A comparison between the prior art devices such as seen in FIG. 4, and the device of the invention shows that the prior art devices such as device 12 of FIG. 4 have axial offsets 220, 221 which is less than the offsets 120, 121 of the device of FIG. 5 of this invention. Comparison also shows that the lever arm 70 of the device of FIG. 5 is, and can always be greater in length than the lever arm 75 of the prior art axially in-line arrangement of FIG. 4, e.g. by at least the incremental distance shown at 74 in FIG. 5(C). This distance 74 extends from longitudinal axis 38 to the hole 85 in the base portion of the manipulation member.

The offset distance 220 of the prior art device of FIG. 4 is limited to a distance of less than one half of the instrument outline 34. This restriction results in devices with only limited leverage being available. Limited leverage is disadvantageous, especially in manipulating large organs and anatomic parts. On the other hand, the offset distances 120, 121 in the dual pivot device of this invention shown in FIG. 5 can be as much as one half the diameter of the outline and even more, while avoiding protrusion of the linking mechanism members 87, 87' outside of the outline 43 of the instrument.

The above described lever arm relationship of manipulation member 90 also applies to manipulation member 92 as indicated at 70' in FIG. 5a. With the above described dual pivot post configuration, movement of push rod 60 in the direction 72 shown in FIG. 5c causes transverse push rod pivot 89 to move in the same direction, and results in rotation of manipulation members 90, 92 in the directions indicated at 140, 141 in FIG. 5c. Due to the extended lever arms 70, 70' hereinbefore described an increased leverage is developed which results in increased pressure on an organ or vessel positioned adjacently in contact with edges 103, 105. This increased pressure through the utilization of two pivot posts is attainable without any increased protrusion of the mechanism outside of the outline 43 of the laparoscopic instrument. This is due in part to the configuration of the manipulation members 90, 92 whereby the base members 107, 109 thereof have a width 150, 151 which is less than the width 160, 161 of the forward edged portions 100, 101 as shown in FIGS. 5(A)-1, 5(B)-1, the top plan view of FIG. 6, the rear sectional elevation view of FIG. 7 and the partial perspective view of FIG. 8. In the embodiment shown, the width of the members 107, 109 is slightly less than one-half the width of the forward edged members 100, 101. As also shown in FIGS. 5A, 5(A)-1, 5(B), 6, 7 and 8, the base members 107, 109 have respective slots 170, 171 which receive the end portions 175, 175' of link members 87, 87' which are remote from pivot 89 of the flattened portion 62 of push-rod 60. The end portions 175, 175' of link members 87, 87' are pivotally engaged at holes 85, 85' by pins 88, 88'. Since the widths of base members 107, 109 are less than the full width of the forward edged portions 100, 101, recesses 190, 191 are established laterally adjacent and inward from the base members 107, 109. These recesses 190, 191 respectively receive base members 107, 109 of manipulation members 90, 92 in the course of their pivotal movement during opening and closing of the end effector 40, thus eliminating any interference due to the utilization of dual transverse pivot posts 47, 47' which are aligned in a plane transverse to longitudinal axis 38.

Figure 10:
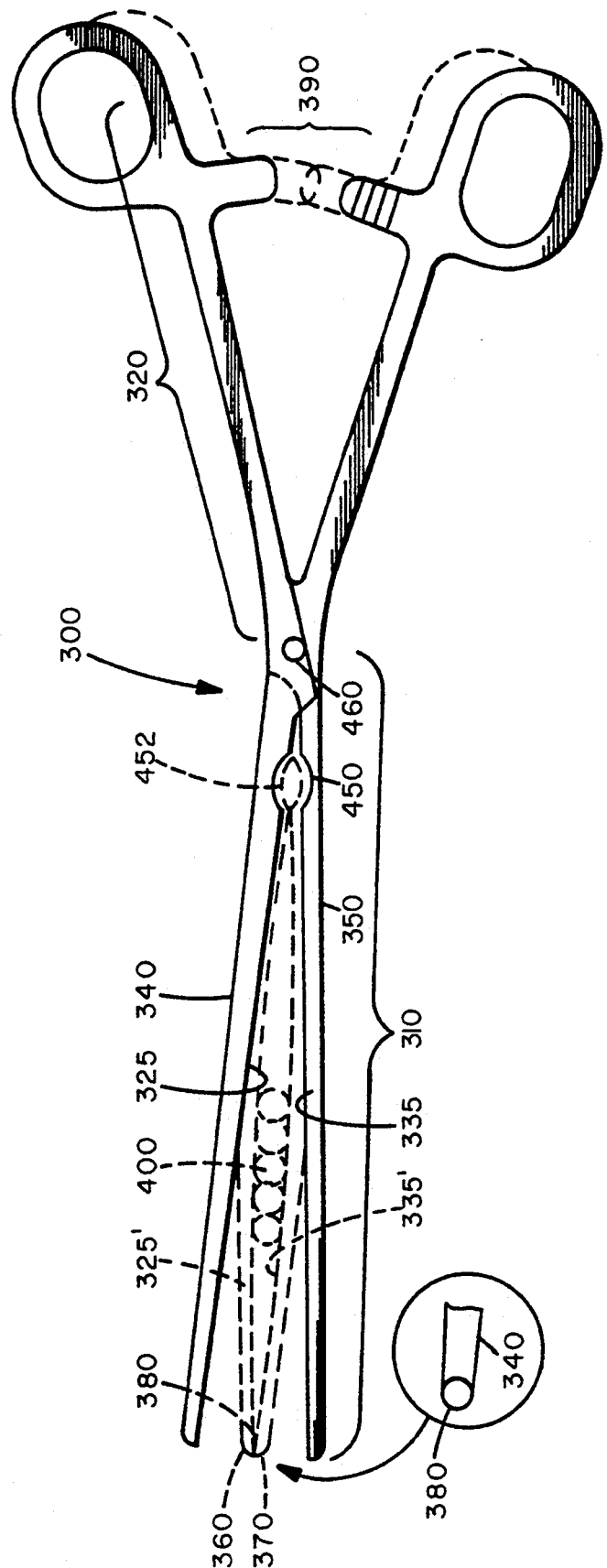
FIG. 10 is an illustration of a prior art non-laparoscopic single pivot colo-rectal bowel clamp.

The present invention is a combination of the aforedescribed dual pivot linkage system with an end effector for use as a bowel clamp. A bowel clamp must be able to gradually develop a substantial pressure on the bowel to prevent leakage while not compressing the tissue to the extent that it is damaged. Manual single pivot bowel clamps 300 of the prior art shown in FIG. 10 can be used to achieve this result in non-laparoscopic procedures, but the length of the clamp blades 310 which is necessary to achieve satisfactory clamping pressure, e.g. 5 to 6 inches, and handle lengths 320 of about 4 inches with a handle spread distances of about 1½ inches preclude the use of the device of this type in laparoscopic procedures. The "phantom" position in FIG. 10 is a typical position of the prior art device 300 for clamping a bowel 400 enclosed between opposite and outwardly bowed intermediate sections 325, 335 of the blades 340, 350, and with end portions 360, 370 of the device 300 being in compressible contact at 380 where the opposed inner surfaces of the blades form the flat resiliently deformed contact region 380. The customary ratchet mechanism 390 is engageable in the "phantom" position to maintain the pressure exerted on bowel portions 400 by gripper blades 340, 350. Cut out regions 450, 452 are provided to reduce the danger of pinching of the bowel near the pivot 460.

With the present invention, as shown in FIGS. 11a and 11b a bowel clamp end effector 40' is shown with gripper blades 90', 92' of about one-half the length of the gripper blades 340, 350 i.e. about 2½ to 3 inches in length (the length sizes of 90', 92' and 340, 350 being to scale and proportional in FIGS. 10 and 11a of the drawings). The bowel clamp can be employed with the dual pivot mechanism of the invention as shown in FIGS. 11a and 11b since the compressive force between the blades 90', 92' is, upon movement of push rod 60' in the direction 72' by actuation of actuating means 50 (FIG. 1) of laparoscopic instrument 10, comparable to that obtained between the longer blades 340, 350 of the larger, non-laparoscopic prior art device. Blades 90', 92' each have outwardly bowed intermediate sections 325'', 335'' which compressibly seal bowel 400'. The blades 90' and 92' may be knurled or serrated to enhance gripping as indicated at 375. Flattened contact region 380' between end portions 360', 370' of resilient gripping blades 90', 92' enables the gradual application of pressure and pressure relief on bowel 400'. Cutout regions 450', 452' of gripping blades 90', 92' adjacent clevis 30' and the extended portion 454 thereof between pivot rods 45, 47 eliminates the danger of pinching the bowel near the pivots.

In the preferred embodiment, blades 90' and 92' are comprised of 17/4 or 17/7 stainless steel. Alternatively, the blades may be made of Carpenter 455 or other materials that will flex enough to provide the desired clamping action. In addition, the blades preferably have dimensions in the following ranges:

length from pivots 45', 47' to ends 380': 2.4–2.6 in.
height (thickness) of blade at pivots 45' 47': 1/16–⅛ in.
height (thickness) of blade 0.5 in. from pivots: 3/32–⅛ in.
height (thickness) of blade 0.75 in. from pivots: 1/32–1/16 in.
height (thickness) of blade at blade tip: 1/32–3/32 in.
width of blade (for 10 mm instrument): 5/32–¼ in.
bow between blade middles when blade tips touch: 0.05–0.10 in.
bow 0.5 in from blade tip when blade tips touch: 0.03–0.06 in.
bow between blades at cut-out region 450', 452': 0.06–0.12 in.
bow between blades directly in front of cut-out: 0.03–0.06 in.

It will be appreciated that with the dimensions and materials as set forth, application of force via actuation of the actuation means (which force can act suitably on the blades due to the dual pivot linkage system) causes the bow between the blades to substantially disappear, except at the cut-out region where a bow of 0.02–0.04 inches is maintained due to the undercut itself.

There bas been described and illustrated herein a disposable colo-rectal laparoscopic bowel clamp instrument. While particular embodiments of the invention have been described, it is not intended that the invention be limited exactly thereto, as it is intended that the invention be as broad in scope as the art will permit. Thus, while various materials were described as being preferred for various parts, it will be appreciated that other materials could be utilized. Similarly, while the blade of the colo-rectal laparoscopic instrument were described as being of a particular length, thickness, bow, etc., it will be appreciated that small changes can be made to the various dimensions without impacting too severely on the functioning of the instrument. Therefore, it will be apparent to those skilled in the art that other changes and modifications may be made to the invention as described in the specification without departing from the spirit and scope of the invention as so claimed.

What is claimed is:

1. A surgical instrument for the manipulation of remotely located internal body parts, said instrument comprising:

a) a longitudinally extending push rod having a first end portion and a second end portion remote from said first end portion, said first end portion having a through-hole substantially on a longitudinal axis of said push rod;

b) a longitudinally extending tube surrounding said push rod along most of its length between said first and second end portions thereof;

c) actuating means engaging said push rod at said second end thereof for imparting reciprocal axial longitudinal motion to said push rod relative to said tube;

d) a clevis means affixed to said tube for engaging the tube adjacent said first end of said push rod;

e) first and second post means engaging said clevis means, with said first post means transverse to the longitudinal axis of said push rod and radially displaced from said longitudinal axis, and said second post means transverse to said longitudinal axis and radially displaced from said longitudinal axis in a direction opposite to the radial displacement of the first post means, said first and second post means being spaced from said first end of said push rod in a direction opposite to the second end of said push rod;

f) clamping means for clamping said body parts having first and second blade members, said first and second blade members each having a forwardly extending portion and a rearwardly extending base portion, with each said rearwardly extending base portion having a through-hole located on another side of said longitudinal axis than the forwardly extending portion of the same blade member, said first and second blade members being respectively pivotally mounted on said first and second post means at intermediate locations between the forwardly extending portions and the base portions of the respective blade members with the forwardly extending portions of the blade respective members being oppositely disposed, and each said forward portion having an outwardly bowed inside intermediate section, a resiliently flattenable forward end portion and an inner cut-away portion adjacent to said clevis means, said inner cut-away portion extending between the first and second post means;

g) first and second connecting means for engaging said blade members, each having first and second oppositely extending terminal portions, one of said first and second connecting means engaging with one of its terminal portions the through-hole of the first end of the push rod and engaging with the other of its terminal portions the through-hole in the base portion of one of said first and second blade members, and the other of said first and second connecting means engaging with one of its terminal portions the through-hole of the end of the push rod and engaging with the other of its terminal portions the through-hole in the base portion of the other one of said first and second blade members.

2. A surgical instrument according to claim 1, wherein:
said tube, clevis means, and push rod are formed of aluminum or aluminum base alloys.

3. A surgical instrument according to claim 1, wherein:
each of said blade members has a length from where said blade member is pivotally mounted on said post means to a tip of said blade member of approximately 2.4 to 2.6 inches, and said intermediate sections of said blade members are bowed such that when said tips of said blade members are touching without force being applied to said actuating means, a portion of said blade members are displaced at least approximately 0.05 inches from each other in a direction perpendicular to said longitudinal axis.

4. A surgical instrument according to claim 1, wherein:
said blade members are formed of stainless steel.

5. A surgical instrument according to claim 1, wherein:
each said base portion has a width slightly less than one-half a width of said forwardly extending portion.

6. A surgical instrument according to claim 5, wherein:
each said base portion further comprises a slot into which the terminal portion of a respective said connecting means fits.

7. A device for connecting a pair of first and second blade members of a clamping device to a push rod arranged within a tube of a surgical instrument, comprising:

a) clevis means for engaging the tube of the surgical instrument adjacent an end of the push rod;

b) first and second pivot posts engaging said clevis means for respectively pivotably engaging said first and second blade members, said first and second pivot posts extending transverse to a longitudinal axis of the push rod and respectively positioned on opposite sides of said longitudinal axis and displaced therefrom;

c) first connecting means for engaging said first blade member at a location along said first blade member on the opposite side of said longitudinal axis to where said first pivot post engages said first blade member, for coupling said first blade member to said push rod, and for enabling pivotal movement of said first blade member; and d) second connecting means for engaging said second blade member at a location along said second blade member on the opposite side of said longitudinal axis to where said second pivot post engages said second blade member, for coupling said second blade member to said push rod, and for enabling pivotal movement of said second blade member, said first and second blade members having respective forward extending opposed resilient gripping portions and respective base portions integral with said forward extending portions, each said forward portion having an outwardly bowed inside intermediate section, a resiliently flattenable forward end portion and an inner cutaway portion adjacent to said clevis means, said inner cut-away portion extending between said first and second pivot posts, said base portions being at an oblique angle with said forward extending portions.

8. Device according to claim 7, wherein:
said first and second blade members have respective forward extending opposed edged portions and respective base portions integral with said forward extending edged portions, said base portions being at an oblique angle with said forward extending edged portions.

9. Device according to claim 8, wherein:

each of said base portions have a width which is less than that of the forward edged portion with which it is integral.

10. Device according to claim 9, wherein:
each said base portion has a recess to receive the other base portion.

11. Device according to claim 10, wherein:
each said base portion extends toward the longitudinal axis of the push rod at an oblique angle with respect to forward edged portion with which it is integral.

12. Device according to claim 11, wherein:
said base member of said first blade member has a slot to receive said first connecting means, and said base member of said second blade member has a slot to receive said second connecting means.

13. Device according to claim 12, wherein:
said first and second blade members are substantially identical and are arranged with their respective recesses oppositely adjacent.

14. Device according to claim 13, wherein:
each base member has a width less than one half a width of a forward extending edged portion.

15. A disposable laparoscopic surgical instrument for the manipulation of remotely located internal body parts, said instrument comprising:
 a) a longitudinally extending push rod having a first end portion and a second end portion remote from said first end portion, said first end portion having a through-hole substantially on the longitudinal axis of said push rod;
 b) a longitudinally extending tube surrounding said push rod along most of its length between said first and second end portions thereof;
 c) actuating means engaging said push rod at said second end thereof for imparting reciprocal axial longitudinal motion to said push rod relative to said tube;
 d) first and second parts coupled to and fixed relative to said longitudinally extending tube, with said first post transverse to the longitudinal axis of said push rod and radially displaced from said longitudinal axis, and said second post transverse to said longitudinal axis and radially displaced from said axis in a direction opposite to the radial displacement of the first post, said first and second posts being spaced from said first end of said push rod in a direction opposite to the second end of said push rod;
 e) clamping means for clamping the body parts having first and second blade members, said first and second blade members each having a forwardly extending portion and a rearwardly extending base portion, with each said rearwardly extending base portion having a through-hole located on the other side of said longitudinal axis than the forwardly extending portion of the same blade member, said first and second blade members being respectively pivotally mounted on said first and second posts at intermediate locations between the forwardly extending portions and the base portions of the respective blade members with the forwardly extending portions of the blade respective members being oppositely disposed, and each said forward portion having an outwardly bowed inside intermediate section, a resiliently flattenable distal portion, and an inner cut-away proximal portion, the length of each of said blade members from where said blade members are pivotally mounted on said posts to tips of the resiliently flattenable distal-portions of said blade members is at least approximately 2.4 inches, and said intermediate sections of said blade members are bowed such that when said tips of said blade members are touching without force being applied to said actuating means, a portion of said blade members are displaced at least approximately 0.05 inches from each other in a direction perpendicular to said longitudinal axis;
 f) first and second connecting means for engaging said blade members each having first and second oppositely extending terminal portions, one of said first and second connecting means engaging with one of its terminal portions the through-hole of the first end of the push rod and engaging with the other of its terminal portions the through-hole in the base portion of one of said first and second blade members, and the other of said first and second connecting means engaging with one of its terminal portions the through-hole of the end of the push rod and engaging with the other of its terminal portions the through-hole in the base-portion of the other one of said first and second blade members.

16. A disposable laparoscopic surgical instrument according to claim 15, wherein:
said tube and push rod are formed of aluminum or aluminum base alloys.

17. A disposable laparoscopic surgical instrument according to claim 16, further comprising:
 g) a clevis means for coupling said first and second posts to said longitudinally extending tube, said clevis means being affixed to said longitudinally extending tube adjacent said first end of said push rod, and receiving said first and second posts.

* * * * *